(12) United States Patent
Geiser et al.

(10) Patent No.: US 7,494,480 B2
(45) Date of Patent: Feb. 24, 2009

(54) DEVICE FOR ADMINISTERING AN INJECTABLE PRODUCT IN DOSES

(75) Inventors: Simon Geiser, Langenthal (CH); Hanspeter Heiniger, Lotzwil (CH); Gilbert Schiltges, Kirchberg (CH)

(73) Assignee: Disetronic Licensing AG, Burgdorf (CH)

( * ) Notice: Subject to any disclaimer, the term of this patent is extended or adjusted under 35 U.S.C. 154(b) by 408 days.

(21) Appl. No.: 10/417,795

(22) Filed: Apr. 17, 2003

(65) Prior Publication Data

US 2004/0006310 A1 Jan. 8, 2004

Related U.S. Application Data

(63) Continuation of application No. PCT/CH01/00471, filed on Jul. 31, 2001.

(30) Foreign Application Priority Data

Oct. 17, 2000 (DE) .................................. 100 51 371

(51) Int. Cl.
*A61M 37/00* (2006.01)
(52) U.S. Cl. ..................................................... 604/131
(58) Field of Classification Search ................ 202/237; 604/152, 187, 151, 131, 200, 202, 156, 205
See application file for complete search history.

(56) References Cited

U.S. PATENT DOCUMENTS

| 3,858,581 | A | * | 1/1975 | Kamen | 604/155 |
|---|---|---|---|---|---|
| 5,112,317 | A | * | 5/1992 | Michel | 604/208 |
| 5,178,609 | A | * | 1/1993 | Ishikawa | 604/131 |
| 5,370,629 | A | | 12/1994 | Michel et al. | |
| 5,643,214 | A | * | 7/1997 | Marshall et al. | 604/134 |
| 5,688,250 | A | * | 11/1997 | Naganuma | 604/200 |
| 5,823,998 | A | * | 10/1998 | Yamagata | 604/131 |
| 5,921,963 | A | * | 7/1999 | Erez et al. | 604/192 |
| 5,968,015 | A | | 10/1999 | Yamamoto | |
| 6,375,638 | B2 | * | 4/2002 | Nason et al. | 604/132 |

FOREIGN PATENT DOCUMENTS

DE 19717107 A1 11/1998

* cited by examiner

*Primary Examiner*—Nicholas D Lucchesi
*Assistant Examiner*—Christopher D Koharski
(74) *Attorney, Agent, or Firm*—Dorsey & Whitney LLP

(57) ABSTRACT

A device for administering an injectable product in doses including a casing, a container for the product, accommodated by the casing, from which container product is delivered through an opening of the container by moving a piston accommodated in the container toward the opening, and a drive for causing the delivery of the product wherein the drive moves the container relative to the casing and the piston.

6 Claims, 2 Drawing Sheets

DEVICE FOR ADMINISTERING AN INJECTABLE PRODUCT IN DOSES

CROSS-REFERENCE TO RELATED APPLICATIONS

This application is a continuation of International Patent Application No. PCT/CH01/00471, filed on Jul. 31, 2001, which claims priority to German Application 10051371.9, filed on Oct. 17, 2000, the contents of both are incorporated herein in their entirety by reference.

BACKGROUND

The invention relates to devices, including infusion apparatus, for administering an injectable product in doses. The application claims the priority of German patent application No. 100 51 371.9, filed on Oct. 17, 2000, with the German Patent and Trademark Office.

Portable injection and/or infusion apparatus are used for administering medicines in fluid form, in particular in liquid form, for example insulin. The medicinal fluid is displaced in doses from a fluid container by means of a piston, and administered. Such apparatus have a broad application in insulin treatment, as pump apparatus and manually operated injection pens. One example of an injection pen is known from WO 93/16740. The insulin pumps of Disetronic Medical Systems AG are examples of portable infusion apparatus. In general, the user constantly carries the apparatus about his/her person, for example, in the workplace or on holiday. In order to be as independent of an external supply as possible and to have freedom of movement, the apparatus should be able to hold as much medicinal fluid as possible but still be as small or compact as possible. Space-saving and convenience is generally desirable in the medical field, including for stationary apparatus and systems.

WO 98/47552 discloses a device for administering an injectable product in doses which comprises a casing, a container accommodated by the casing, from which a product dosage is delivered through an opening of the container by an advancing toward the opening a piston accommodated in the container, and a drive means. The piston is slidably moved toward the opening of the container by means of a driven member of the drive means. The drive means comprises a number of telescopic sliding stages.

SUMMARY

It is one object of the present invention to provide a device for administering an injectable product in doses, which assists in saving space and therefore is suitable as a device for a portable medicine administering apparatus.

In one embodiment of the present invention, this object is addressed by providing a device for administering an injectable product in doses including a casing, a container for the product, accommodated by the casing, from which container product is delivered through an opening of the container by moving a piston accommodated in the container toward the opening, and a drive for causing the delivery of the product wherein the drive moves the container relative to the casing and the piston.

In one embodiment, the device comprises a casing in which a container for an injectable product is accommodated. The container comprises an opening through which product can be delivered and accommodates a piston, wherein a volume is formed in the container between the piston and the opening, the injectable product being situated in the volume. In order to deliver product, preferably in an adjustable product dosage, the volume between the piston and the opening of the container is reduced by means of a drive means. The drive means causes the container and the piston to slide relative to each other. In accordance with the invention, this is achieved by sliding the container relative to the casing. The container is moved by the drive means. The container is accommodated by the casing such that it can slide and is mechanically coupled to the drive means. This arrangement leads to new possible designs for administering apparatus. Available spaces in a closed casing can, for example, be more flexibly used than before.

Although in one embodiment the container is slid relative to the casing and the piston is slid relative to the container and the casing, in some embodiments only the container may be moved or slid relative to the casing. These embodiments are also advantageous.

In known injection pens, both dosing and the delivery movement of the piston are performed by a driven member serving as a piston rod, which only contacts the piston during the delivery movement. After delivery, the driven member returns to a dosing position in which a slight gap, which then exists between the piston and the driven member, is reduced by adjusting the driven member and the product dosage to be delivered by the next delivery movement of the driven member, thus setting a dose. Using the arrangement of the present invention, the delivery movement can be separated from the dosing movement in such injection pens. The dosing movement can still be performed by a driven member of the drive means, while the delivery movement is performed by the container. If, however, a driven member of the drive means acting on the piston is also moved during the delivery movement, such as in some preferred embodiments, a telescopic effect is achieved alone by the driven member moved and the container moved counter to it, when the container is pushed via a supporting member for the driven member. Including the container in the movement necessary for delivery, or performing this movement using only the container, can also achieve design flexibility. In addition, this provides freedom in the form and arrangement of the drive means.

The piston is prevented from sliding together with the container, such that the gap between the piston and the container opening is reduced, as required for delivering the product. In some embodiments, the piston can be fixedly connected to the casing, for example via a holding element. In some preferred embodiments, a driven member of the drive means, protruding into the container, supports the piston.

In one preferred embodiment, the piston is slid relative to the casing, in the advancing direction, by the driven member. When delivering product, the driven member presses against the piston in the advancing direction. The movement of the piston relative to the container is thus composed of two partial movements, wherein a first partial movement is generated by sliding the container and a second partial movement is generated by sliding the piston by means of the driven member. A shorter driven member, as compared with the prior art, can be used for sliding the piston.

In some embodiments, the two partial movements are preferably performed simultaneously. In this way, the driven member is slid relative to the casing in the advancing direction of the piston and the container is slid relative to the casing, counter to the advancing direction of the piston. The driven member and the container may preferably move at the same sliding speeds, i.e., in this case, they slide in diametric opposition.

In one embodiment, the drive means preferably comprises at least two sliding stages, movable relative to each other and relative to the casing, and preferably telescopic. In addition to a first sliding stage, at least a second sliding stage is provided which slides in the advancing direction of the piston, relative to the casing and also relative to the first sliding stage, and which slaves the first sliding stage when it slides in the advancing direction of the piston. By combining a number of sliding stages with the sliding of the container, which serves as an additional sliding stage, the length of each of the individual sliding stages can be shortened as compared with the prior art. Conversely, if sliding stages of equal length are used, as in prior art, a longer sliding path can be achieved, such that longer containers can be used. A device in accordance with the invention, for administering the injectable product in doses, can either accommodate more injectable product for the same length, or can be designed smaller for the same amount of product.

In some embodiments, the driven member or the number of sliding stages are supported on a supporting member and can be moved relative to the supporting member. The supporting member is a component of the drive means. At the end of delivery, the supporting member and the driven member protrude into the container. When slid, the container is pushed over the supporting member which cannot be slid relative to the casing. The driven member can simultaneously slide the piston in the advancing direction towards the opening of the container or merely support the piston against sliding together with the container. In an alternative embodiment, the supporting member can also be slid in the advancing direction, relative to the casing, into the container.

The container and/or the driven member can be slid manually or using motors. The container can be connected to a toothed rack which can be driven via a toothed wheel. In one preferred embodiment, the container is driven by a spindle which is a component of the drive means and is rotary driven. The container is mounted in the casing such that it can slide but is secured against rotating, and is connected to the spindle by means of a screw joint. When the spindle is rotated, the container slides along the spindle. The container is fixed to a pusher which, together with the spindle, forms the screw joint. The container may be directly fixed to a spindle nut which forms part of the screw joint. The spindle ia arranged longitudinally alongside the container. In this way, sliding the container and the driven member simultaneously is simple. The pusher is fixed to a head region of the container. The spindle could also be arranged below the container, which however may enlarge the space requirement with regard to the longitudinal extension of the device. Although less preferred, the spindle could also be fixedly connected to the container and engage with a spindle nut driven by the drive means.

In some embodiments, the movements of the container and the driven member can each be generated by a drive means of their own. However, in some preferred embodiments, the container and the driven member are driven by a common drive means. A manual or a motorized drive means can be provided. In one preferred embodiment, the drive means comprises a motor, which enables the product to be automatically delivered in doses. The motor drives the container and the driven member via a distributor gear. It is, however, also possible to provide a motor for each of the container and the driven member, in order to enable the product to be delivered in finer doses by non-simultaneously driving the container and the driven member.

If the motor is arranged alongside the container, this leads to a particular saving in length. The motor is situated, at least in an end position of the delivery movement of the container and the driven member, level with the container. In some embodiments, the motor is preferably accommodated by the casing of the device, secured against sliding and rotating. It can also, however, be moved together with the container or the driven member.

Sliding the container is preferred in some embodiments of pump apparatus in accordance with the present invention. It can also, however, be advantageous in an injection pen. If the drive means is arranged behind the container, the drive means can be slid, together with the driven member, into the container. If a drive means is used which is fixed to the casing, the container can pass over the drive means. A particularly space-saving arrangement is thus ensured.

Although the invention primarily has its application in portable infusion and/or injection apparatus, it can also be advantageously used in stationary systems. Typically, the product to be delivered or administered is a medically or cosmetically active product, for example, insulin.

BRIEF DESCRIPTION OF THE DRAWINGS

Exemplary embodiments, including preferred embodiments, of the invention will now be explained in conjunction with the accompanying drawings.

DETAILED DESCRIPTION

Figure 1:
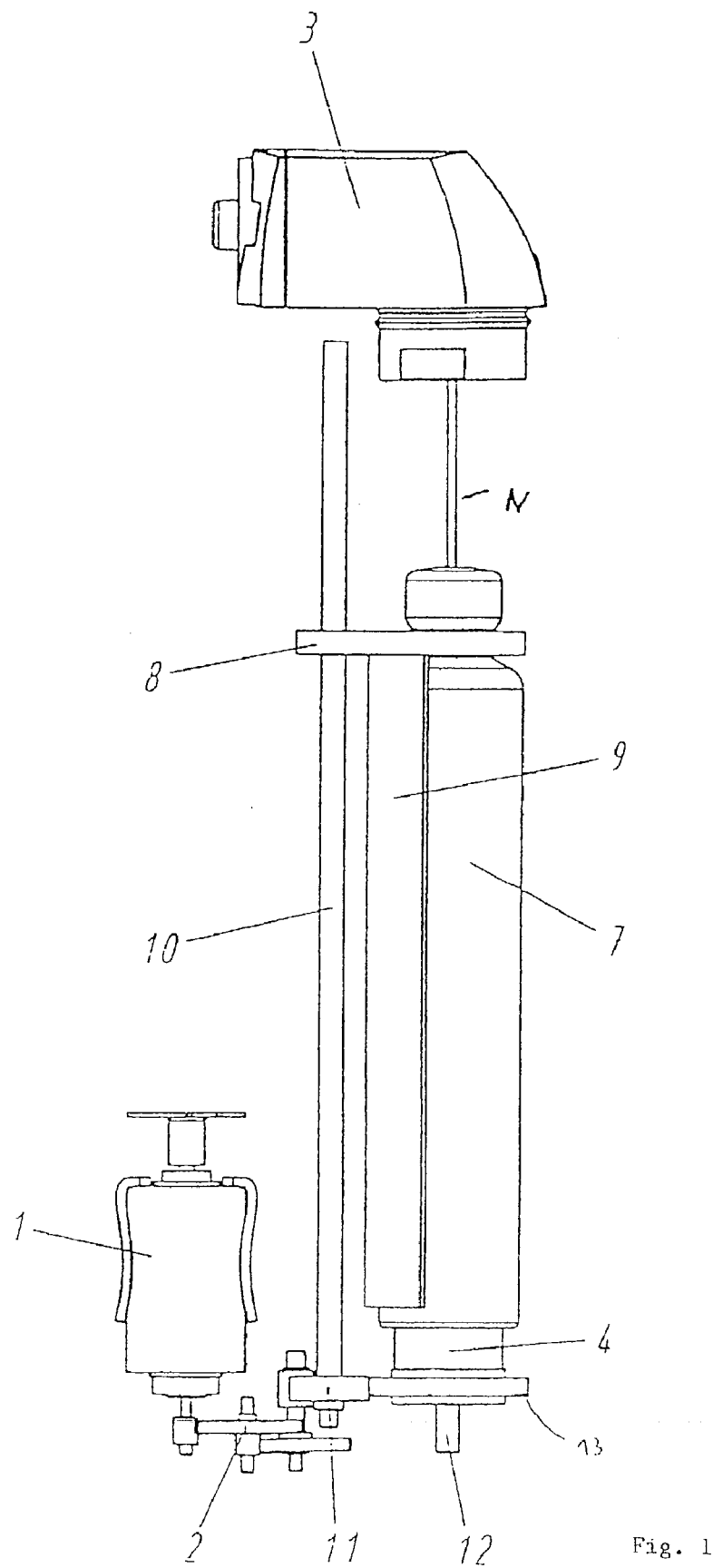
FIG. 1 is a side view of device for administering an injectable product in doses in accordance with the present invention.
Figure 2A:
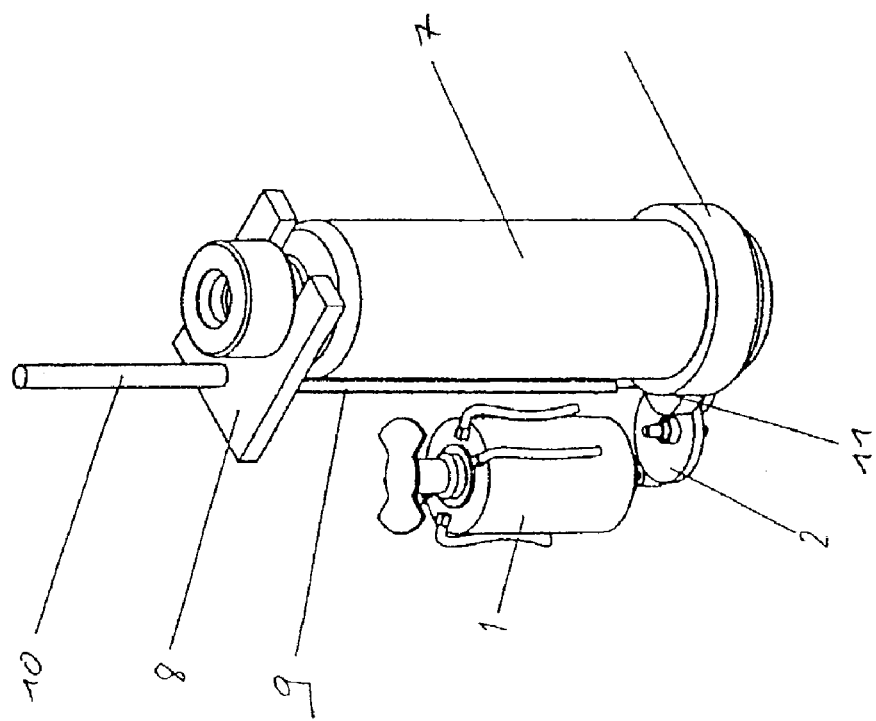
FIG. 2a depicts a device in accordance with the invention, shown in an intermediate position.

FIGS. 1 and 2 show a device in accordance with the invention, wherein for reasons of clarity the casing is not shown. A motor 1 of a drive means is accommodated in the casing, secured against sliding. The motor drives a spindle 10 and a supporting member 4 via toothed wheels 2, 11 and 13. The supporting member 4 protrudes into a container 7 from behind. A driven member 4a, which can be seen in FIG. 2a, supported on the supporting member 4, presses against a piston which is accommodated in the container 7 such that it can slide. In some embodiments, the container 7 is preferably an ampoule. It comprises an opening at its front end, the opening usually being sealed by a membrane. The membrane can be pierced by an injection needle N and thus establishes a connection between the container 7 and the patient. The connection can also be lengthened via a catheter. When the piston is slid relative to the container 7 towards the opening, product is delivered through the opening.

Together with the supporting member 4, the driven member 4a forms a spindle drive. Rotating the toothed wheel 13 slides the driven member 4a in the advancing direction of the piston. The piston thus moves relative to the casing towards the opening of the container 7.

The container 7 is mounted in the casing such that it can slide linearly. A pusher 8 establishes a connection between the spindle 10 and the container 7. The container 7 also comprises a radial notch in its head region, via which the container 7 is inserted into a U-shaped indentation in the pusher 8. The pusher 8 is thus connected to the container 7, secured against sliding. The pusher 8 itself comprises a thread or is connected to a threaded part, preferably a nut. The pusher 8 and the spindle 10 form a screw joint, i.e., a spindle drive. When the spindle 10 is rotated, the pusher 8 and the container 7 are slid in such a way that the piston slides relatively towards the container opening. The sliding of the piston within the container 7 is thus composed of two partial movements: on the one hand, the container 7 sliding counter to the advancing direction of the piston and, on the other, the piston sliding in the advancing direction relative to the casing.

The container 7 is shown in FIG. 1 in a middle position. In the depicted exemplary embodiment, a needle holder 3 is fixedly connected to the casing. A needle N is provided, having a sufficient length for the needle N to penetrate the membrane of the container 7 in all the sliding positions of the container 7. A flexible hose can also be provided, which compensates for movement of the container 7.

FIG. 2a shows a three-dimensional representation of the device in accordance with FIG. 1, in a position after the delivery of product fluid has begun. The container 7 has already been slid by the distance 10a counter to the advancing direction of the piston. The driven member 4a has already been pushed some way into the container 7 in the advancing direction of the piston.

Figure 2B:
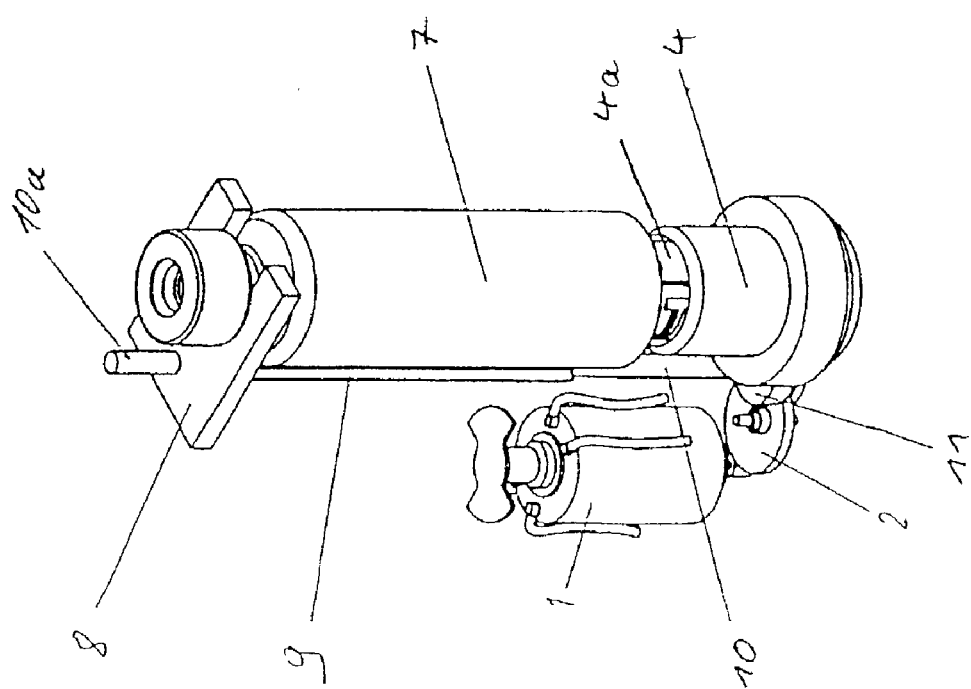
FIG. 2b depicts a device in accordance with the invention, shown in an end position.

FIG. 2b shows the device in an end position. The container 7 and the driven member 4a have reached their foremost sliding positions. The piston has been maximally slid towards the opening of the container 7.

Before the product fluid is delivered, the container 7 is inserted into the pusher 8 from the side. Together with an abutting piece 9, the pusher 8 forms a container mount. For delivering the product, the rotational movement of the motor 1 is transferred to the supporting member 4. The driven member 4a is moved or slid in the advancing direction of the piston via the threaded engagement with the supporting member 4. The rotation of the spindle 10 coupled to the intermediate wheel 11 slides the pusher 8 towards the intermediate wheel 11. This moves the container 7 counter to the advancing direction of the piston. The abutting piece 9 serves to stabilize the movement of the container 7. During delivery, the container 7 moves in diametric opposition to the extending driven member 4a and is slipped over the non-translating supporting member 4. Once delivery of the product fluid is complete, the driven member 4a and the container 7 can be returned again to their starting positions by changing the rotational direction of the motor 1.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering an injectable product in doses, the device comprising:
    a casing;
    a container for the product accommodated within the casing, the container having a dispensing end;
    a piston slidably coupled in another end of the container, the piston slidable in an advancing direction to deliver the product;
    a pusher coupled to the dispensing end of the container;
    a spindle drive rotatably coupled to the pusher, the spindle drive comprising a rotatable spindle, the spindle drive configured to displace the pusher along the spindle counter to the advancing direction, such that the pusher slides the container relative to the casing and the piston, counter to the advancing direction, causing product to be dispensed; and
    a motor coupled to the spindle drive, the motor driving a rotational movement of the spindle drive.

2. The device as set forth in claim 1, wherein a driven member of said rotary driven spindle protrudes into the container and supports the piston.

3. The device as set forth in claim 2, wherein the driven member is slid relative to the casing, toward the opening.

4. The device as set forth in claim 2, wherein the rotary driven spindle comprises at least two telescopic sliding stages.

5. The device as set forth in claim 1, wherein the rotary driven spindle comprises a driven member and a supporting member, the driven member supported on said supporting member and movable relative to the supporting member, wherein the supporting member and the driven member, when slid, are slid into the container.

6. The device as set forth in claim 1, wherein the rotary driven spindle comprises a driven member and a supporting member, the driven member supported on said supporting member and movable relative to the supporting member, wherein, when the supporting member and the driven member are slid, the container is slid over the driven member and at least partially also over the supporting member.

* * * * *

UNITED STATES PATENT AND TRADEMARK OFFICE
CERTIFICATE OF CORRECTION

PATENT NO. : 7,494,480 B2
APPLICATION NO. : 10/417795
DATED : February 24, 2009
INVENTOR(S) : Simone Geiser et al.

Page 1 of 1

It is certified that error appears in the above-identified patent and that said Letters Patent is hereby corrected as shown below:

|  | DELETE | INSERT |
|---|---|---|
| On the Title page, item [75]: Inventors: | "Simon Geiser" | -- Simone Geiser -- |

Signed and Sealed this

Fourteenth Day of April, 2009

JOHN DOLL
*Acting Director of the United States Patent and Trademark Office*